(12) United States Patent
Medepalli et al.

(10) Patent No.: US 9,132,103 B2
(45) Date of Patent: Sep. 15, 2015

(54) DISINFECTING AGENT COMPRISING EUGENOL, TERPINEOL AND THYMOL

(75) Inventors: Srilaxmi Venkata Medepalli, Bangalore (IN); Amit Chakrabortty, Bangalore (IN); Bharat Cheviti, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/496,894

(22) PCT Filed: Sep. 3, 2010

(86) PCT No.: PCT/EP2010/062982
§ 371 (c)(1),
(2), (4) Date: Mar. 19, 2012

(87) PCT Pub. No.: WO2011/036048
PCT Pub. Date: Mar. 31, 2011

(65) Prior Publication Data
US 2012/0276022 A1 Nov. 1, 2012

(30) Foreign Application Priority Data
Sep. 24, 2009 (IN) .......................... 2220/MUM/2009

(51) Int. Cl.
| | | |
|---|---|---|
| *A01N 31/06* | (2006.01) |
| *A01P 1/00* | (2006.01) |
| *A61K 8/34* | (2006.01) |
| *A61Q 11/00* | (2006.01) |
| *C11D 3/20* | (2006.01) |
| *C11D 3/48* | (2006.01) |
| *A61K 31/05* | (2006.01) |
| *A01N 31/04* | (2006.01) |
| *A01N 31/08* | (2006.01) |
| *A01N 31/16* | (2006.01) |
| *A61K 31/045* | (2006.01) |

(52) U.S. Cl.
CPC .............. *A61K 31/05* (2013.01); *A01N 31/04* (2013.01); *A01N 31/08* (2013.01); *A01N 31/16* (2013.01); *A61K 31/045* (2013.01)

(58) Field of Classification Search
None
See application file for complete search history.

(56) References Cited

U.S. PATENT DOCUMENTS

| | | |
|---|---|---|
| 658,596 A | 9/1900 | Simpson |
| 2,196,763 A | 4/1940 | Figg, Jr. |
| 2,359,241 A | 9/1944 | Partansky |
| 3,256,310 A | 6/1966 | Weil |
| 3,779,932 A | 12/1973 | Jaggers et al. |
| 3,787,566 A | 1/1974 | Gauvreau |
| 4,267,168 A | 5/1981 | Van Leuven |
| 4,474,798 A | 10/1984 | Inagi et al. |
| 4,548,809 A | 10/1985 | Fung |
| 4,966,754 A | 10/1990 | Purohit |
| 4,992,259 A | 2/1991 | Schiraldi et al. |
| 5,013,486 A | 5/1991 | Joshi |
| 5,073,366 A | 12/1991 | Beck |
| 5,283,056 A | 2/1994 | Chung et al. |
| 5,322,638 A | 6/1994 | Schadt et al. |
| 5,472,684 A | 12/1995 | Nabi |
| 5,474,712 A | 12/1995 | Dotolo |
| 5,474,761 A | 12/1995 | Liang |
| 5,591,708 A | 1/1997 | Richter |
| 5,763,468 A | 6/1998 | Barranx et al. |
| 5,817,295 A | 10/1998 | Chaudhari et al. |
| 5,939,050 A | 8/1999 | Iyer |
| 5,942,478 A | 8/1999 | Lopes |
| 5,965,518 A | 10/1999 | Nakatsu et al. |
| 6,048,368 A | 4/2000 | Tcheou et al. |
| 6,048,836 A * | 4/2000 | Romano et al. ............... 510/490 |
| 6,066,674 A | 5/2000 | Hioki |
| 6,114,298 A | 9/2000 | Petri et al. |
| 6,177,388 B1 | 1/2001 | Cheung et al. |
| 6,183,766 B1 | 2/2001 | Sine et al. |
| 6,190,674 B1 | 2/2001 | Beerse et al. |
| 6,210,695 B1 | 4/2001 | Beerse et al. |
| 6,248,705 B1 | 6/2001 | Cardola et al. |
| 6,261,540 B1 | 7/2001 | Nelson |
| 6,277,805 B1 | 8/2001 | Kupneski |
| 6,323,166 B1 | 11/2001 | Kamiya |
| 6,455,086 B1 | 9/2002 | Trinh et al. |
| 6,506,707 B1 * | 1/2003 | Bessette ..................... 504/116.1 |
| 6,521,578 B1 | 2/2003 | Stute et al. |

(Continued)

FOREIGN PATENT DOCUMENTS

| | | |
|---|---|---|
| CH | 692411 | 6/2002 |
| CN | 1669576 | 9/2005 |

(Continued)

OTHER PUBLICATIONS

Burt et al, 2004, Essential oils: their antibacterial properties and potential application in foods—a review, Int J of Food Microbiology, 94, 223-253.

(Continued)

*Primary Examiner* — Frederick Krass
*Assistant Examiner* — Michael P Cohen
(74) *Attorney, Agent, or Firm* — Ronald A. Koatz

(57) ABSTRACT

The present invention relates to a method of disinfecting a surface and to antimicrobial composition, particularly for personal cleaning, oral care, or hard surface cleaning. It is an object of the present invention to provide for an antimicrobial composition that has relatively fast antimicrobial action. The inventors have found that use of small amounts of eugenol in combination with thymol and terpineol enables this fast kinetics at much lower amount of thymol and terpineol than without eugenol.

16 Claims, No Drawings

(56) References Cited

U.S. PATENT DOCUMENTS

| | | |
|---|---|---|
| 6,531,115 B1 | 3/2003 | Singh |
| 6,534,042 B2 | 3/2003 | Delli Santi et al. |
| 6,537,955 B1 | 3/2003 | Raso et al. |
| 6,576,247 B1 | 6/2003 | Ikemoto et al. |
| 6,607,733 B1 | 8/2003 | Diec |
| 6,613,728 B1 | 9/2003 | Sirianni et al. |
| 6,624,126 B1 | 9/2003 | Kasuga |
| 6,645,472 B1 | 11/2003 | Anderson |
| 6,753,305 B2 | 6/2004 | Raso et al. |
| 6,841,090 B1 | 1/2005 | Allighieri et al. |
| 6,861,402 B1 | 3/2005 | Miracle |
| 6,902,726 B1 | 6/2005 | Varel |
| 6,921,745 B2 | 7/2005 | Yamada et al. |
| 7,754,774 B2 | 7/2010 | Kobayashi et al. |
| 8,066,979 B1 | 11/2011 | Dickens |
| 2001/0000029 A1 | 3/2001 | Misumi |
| 2002/0002124 A1 | 1/2002 | Biedermann et al. |
| 2002/0081270 A1 | 6/2002 | Delli Santi |
| 2002/0107287 A1 | 8/2002 | Bessette et al. |
| 2002/0176879 A1 | 11/2002 | Dodd et al. |
| 2002/0182268 A1 | 12/2002 | Bessette et al. |
| 2003/0044441 A1 | 3/2003 | Schmid et al. |
| 2003/0044469 A1 | 3/2003 | Viladot Petit et al. |
| 2003/0077233 A1 | 4/2003 | Suckerman |
| 2003/0129150 A1 | 7/2003 | Pauly et al. |
| 2003/0138394 A1 | 7/2003 | Charrouf et al. |
| 2003/0138502 A1 | 7/2003 | Pauly et al. |
| 2003/0147963 A1 | 8/2003 | De Moragas et al. |
| 2003/0152536 A1 | 8/2003 | Pauly et al. |
| 2003/0231978 A1 | 12/2003 | Franklin et al. |
| 2004/0014818 A1 | 1/2004 | Boeck et al. |
| 2004/0028697 A1 | 2/2004 | Pauly et al. |
| 2004/0042996 A1 | 3/2004 | Pauly et al. |
| 2004/0044078 A1 | 3/2004 | Kawa et al. |
| 2004/0047832 A1 | 3/2004 | Pauly et al. |
| 2004/0067203 A1 | 4/2004 | Parikh |
| 2004/0081714 A1 | 4/2004 | Pauly et al. |
| 2004/0096479 A1 | 5/2004 | Levine |
| 2004/0105836 A1 | 6/2004 | Seipel et al. |
| 2004/0115158 A1 | 6/2004 | Schieferstein et al. |
| 2004/0142007 A1 | 7/2004 | Moussou et al. |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0198630 A1 | 10/2004 | Schmid et al. |
| 2004/0209795 A1 | 10/2004 | Vlad |
| 2004/0234480 A1 | 11/2004 | Pauly et al. |
| 2005/0019353 A1 | 1/2005 | Prinz et al. |
| 2005/0019431 A1 | 1/2005 | Modak et al. |
| 2005/0077497 A1 | 4/2005 | Anderson |
| 2005/0089497 A1 | 4/2005 | Prinz et al. |
| 2005/0089499 A1 | 4/2005 | Moussou et al. |
| 2005/0119153 A1 | 6/2005 | Burt et al. |
| 2005/0143277 A1 | 6/2005 | Dufay et al. |
| 2005/0172859 A1 | 8/2005 | Nieendick et al. |
| 2005/0256021 A1 | 11/2005 | Lu |
| 2006/0008482 A1 | 1/2006 | Prinz et al. |
| 2006/0039956 A1 | 2/2006 | Hensen et al. |
| 2006/0045914 A1 | 3/2006 | Narayanan |
| 2006/0057090 A1 | 3/2006 | Buchwald-Werner |
| 2006/0079414 A1 | 4/2006 | Nieendick et al. |
| 2006/0093570 A1 | 5/2006 | Duddington et al. |
| 2006/0128585 A1 | 6/2006 | Adair et al. |
| 2006/0134013 A1 | 6/2006 | Sharma |
| 2006/0141073 A1 | 6/2006 | Worrell |
| 2006/0153959 A1 | 7/2006 | Behan et al. |
| 2006/0165631 A1 | 7/2006 | Danoux et al. |
| 2006/0165820 A1 | 7/2006 | Yatcilla |
| 2006/0276336 A1 | 12/2006 | Sardo |
| 2007/0014878 A1 | 1/2007 | Gardiner |
| 2007/0053849 A1 | 3/2007 | Doyle et al. |
| 2007/0081966 A1 | 4/2007 | Behler et al. |
| 2007/0104676 A1 | 5/2007 | Moser et al. |
| 2007/0154414 A1 | 7/2007 | Bonfiglio |
| 2007/0218016 A1 | 9/2007 | Rabenhorst et al. |
| 2007/0227930 A1 | 10/2007 | Bromberg et al. |
| 2007/0231295 A1 | 10/2007 | Hoppe |
| 2007/0237847 A1 | 10/2007 | Henry et al. |
| 2007/0258991 A1 | 11/2007 | Buasen et al. |
| 2007/0270321 A1 | 11/2007 | Barnhart et al. |
| 2008/0008660 A1 | 1/2008 | Rabenhorst et al. |
| 2008/0026974 A1 | 1/2008 | Barnhart et al. |
| 2008/0032908 A1 | 2/2008 | Kurtz |
| 2008/0044479 A1 | 2/2008 | Stack |
| 2008/0045491 A1 | 2/2008 | Fitchmun |
| 2008/0051312 A1 | 2/2008 | Lestage et al. |
| 2008/0064711 A1 | 3/2008 | Friedman |
| 2008/0096790 A1 | 4/2008 | Behan et al. |
| 2008/0107742 A1 | 5/2008 | Hare |
| 2008/0118591 A1 | 5/2008 | Natsch |
| 2008/0160000 A1 | 7/2008 | Motozono et al. |
| 2008/0171709 A1 | 7/2008 | Remmal |
| 2008/0194675 A1 | 8/2008 | Bettuzzi |
| 2008/0207480 A1 | 8/2008 | Pipko |
| 2008/0214432 A1 | 9/2008 | Gaudin |
| 2008/0214518 A1 | 9/2008 | Remmal |
| 2008/0214568 A1 | 9/2008 | Remmal |
| 2008/0220036 A1 | 9/2008 | Miltz et al. |
| 2008/0221003 A1 | 9/2008 | Meine et al. |
| 2008/0253976 A1 | 10/2008 | Scott |
| 2008/0274072 A1* | 11/2008 | Manolas et al. ............ 424/76.9 |
| 2008/0299220 A1 | 12/2008 | Tamarkin et al. |
| 2009/0004308 A1 | 1/2009 | Frehner et al. |
| 2009/0035228 A1 | 2/2009 | Modak |
| 2009/0105195 A1 | 4/2009 | O'Brien |
| 2009/0165228 A1 | 7/2009 | Kilkenny et al. |
| 2009/0317431 A1 | 12/2009 | Schaefer |
| 2010/0003198 A1 | 1/2010 | Stolmeier et al. |
| 2010/0061946 A1 | 3/2010 | Scherner et al. |
| 2010/0184855 A1 | 7/2010 | Bernhardt et al. |
| 2011/0223114 A1 | 9/2011 | Chakrabortty et al. |
| 2012/0004641 A1 | 1/2012 | Bruehwiler et al. |
| 2014/0170198 A1 | 6/2014 | Franklin et al. |

FOREIGN PATENT DOCUMENTS

| | | |
|---|---|---|
| CN | 101036459 | 9/2007 |
| CN | 101313772 | 12/2008 |
| CN | 101590287 | 12/2009 |
| CN | 101601382 | 12/2009 |
| CN | 101874531 | 11/2010 |
| CN | 102229861 | 11/2011 |
| DE | 2263126 | 7/1973 |
| DE | 2445676 | 4/1976 |
| DE | 3117792 | 11/1982 |
| DE | 102004038285 | 4/2006 |
| EP | GB2131683 | 6/1984 |
| EP | 0129987 | 11/1986 |
| EP | 0621335 | 10/1994 |
| EP | 715856 | 6/1996 |
| EP | 0916718 | 10/1997 |
| EP | 0916720 | 5/1999 |
| EP | 0948892 | 10/1999 |
| EP | 0950399 | 10/1999 |
| EP | 0966883 | 12/1999 |
| EP | 0995425 | 4/2000 |
| EP | 1146111 | 4/2000 |
| EP | 1013261 | 6/2000 |
| EP | 1170006 | 1/2002 |
| EP | 1079703 B | 8/2002 |
| EP | 0912098 | 4/2003 |
| EP | 1561476 | 8/2005 |
| EP | 1604643 | 12/2005 |
| EP | 1607098 | 12/2005 |
| EP | 1661976 | 5/2006 |
| EP | 1672054 | 6/2006 |
| EP | 1194461 | 10/2008 |
| EP | 2018869 | 1/2009 |
| EP | 2047889 | 4/2009 |
| EP | 2348838 B1 | 5/2013 |
| ES | 2074030 | 8/1995 |
| FR | 861920 | 2/1941 |
| FR | 1137 M | 5/1961 |
| FR | 1137 M | 2/1962 |

(56) References Cited

FOREIGN PATENT DOCUMENTS

| | | |
|---|---|---|
| FR | 861920 | 2/1962 |
| FR | 1356209 | 3/1964 |
| FR | 2697133 | 4/1994 |
| FR | 2752730 | 3/1998 |
| GB | 366870 | 2/1932 |
| GB | 508407 | 6/1939 |
| GB | 1420946 | 1/1976 |
| GB | 2307915 | 6/1997 |
| GB | 2319181 | 5/1998 |
| GB | 2320927 | 7/1998 |
| GB | 2322552 | 9/1998 |
| GB | 2341092 | 3/2000 |
| GB | 2393911 | 4/2004 |
| JP | 2196718 | 3/1990 |
| JP | 03-011013 | 1/1991 |
| JP | 9241139 | 9/1997 |
| JP | H10114636 | 5/1998 |
| JP | 11502539 | 3/1999 |
| JP | 11130642 | 5/1999 |
| JP | 11228368 | 8/1999 |
| JP | 11315012 | 11/1999 |
| JP | 98044959 | 1/2000 |
| JP | 2000026260 | 1/2000 |
| JP | 2000063262 | 2/2000 |
| JP | 2000344641 | 12/2000 |
| JP | 2003113013 | 4/2003 |
| JP | 2003113013 A2 | 4/2003 |
| JP | 2004075798 | 3/2004 |
| JP | 2004123674 | 4/2004 |
| JP | 2004203839 | 7/2004 |
| JP | 20052130 | 1/2005 |
| JP | 2005015368 | 1/2005 |
| JP | 2005065750 | 3/2005 |
| JP | 2005239965 | 9/2005 |
| JP | 2005298357 | 10/2005 |
| JP | 2006095182 | 4/2006 |
| JP | 2006307231 | 11/2006 |
| JP | 2009196987 | 9/2009 |
| JP | 2010037272 | 2/2010 |
| JP | 2012505851 | 3/2012 |
| JP | 2012250937 | 12/2012 |
| KR | 020030181 | 4/2002 |
| KR | 20020030181 | 4/2002 |
| KR | 20020032949 | 5/2002 |
| KR | 100885511 | 2/2009 |
| KR | 100885511 B1 | 2/2009 |
| KR | 20100123424 | 11/2010 |
| KR | 20120093607 | 8/2012 |
| RU | 2228168 | 5/2004 |
| RU | 2263115 | 10/2005 |
| RU | 2277923 | 6/2006 |
| SU | 1644963 | 4/1991 |
| WO | WO9218091 | 10/1992 |
| WO | WO9512379 | 5/1995 |
| WO | WO9611694 | 4/1996 |
| WO | WO9713495 | 4/1997 |
| WO | WO9715277 | 5/1997 |
| WO | WO9725106 | 7/1997 |
| WO | WO9730586 A1 | 8/1997 |
| WO | WO9731092 | 8/1997 |
| WO | WO9731093 | 8/1997 |
| WO | WO9801524 | 1/1998 |
| WO | WO9802044 A1 | 1/1998 |
| WO | WO9802139 | 1/1998 |
| WO | WO9811867 | 3/1998 |
| WO | WO9824314 | 6/1998 |
| WO | WO9844959 | 10/1998 |
| WO | WO9854279 | 12/1998 |
| WO | WO9855080 A2 | 12/1998 |
| WO | WO9855092 | 12/1998 |
| WO | WO9855093 | 12/1998 |
| WO | WO9855094 | 12/1998 |
| WO | WO9855095 A1 | 12/1998 |
| WO | WO9936033 | 7/1999 |
| WO | WO9952360 | 10/1999 |
| WO | WO9958631 | 11/1999 |
| WO | WO0000166 | 1/2000 |
| WO | WO0025763 | 5/2000 |
| WO | WO0051436 | 9/2000 |
| WO | WO0061106 | 10/2000 |
| WO | WO0118201 | 3/2001 |
| WO | WO0167868 | 9/2001 |
| WO | WO0170215 A1 | 9/2001 |
| WO | WO0179409 | 10/2001 |
| WO | WO02065859 | 8/2002 |
| WO | WO02096435 | 12/2002 |
| WO | WO03010273 | 2/2003 |
| WO | WO03034994 | 5/2003 |
| WO | WO03037270 | 5/2003 |
| WO | WO03050224 | 6/2003 |
| WO | WO03091375 | 11/2003 |
| WO | WO03095600 | 11/2003 |
| WO | WO2004006679 | 1/2004 |
| WO | WO2004032886 | 4/2004 |
| WO | WO2004035723 A1 | 4/2004 |
| WO | WO2005094385 | 10/2005 |
| WO | WO2006012715 | 2/2006 |
| WO | WO2006042661 | 4/2006 |
| WO | WO2006053458 A1 | 5/2006 |
| WO | WO2006109898 | 10/2006 |
| WO | WO2007065538 | 6/2007 |
| WO | WO2007110790 A1 | 10/2007 |
| WO | WO2007125216 | 11/2007 |
| WO | WO2007125216 A1 | 11/2007 |
| WO | WO2008017484 | 2/2008 |
| WO | WO2008028278 | 3/2008 |
| WO | WO2008034549 | 3/2008 |
| WO | WO2008035101 | 3/2008 |
| WO | WO2008060130 | 5/2008 |
| WO | WO2008061658 | 5/2008 |
| WO | WO2008085446 | 7/2008 |
| WO | WO2008088827 | 7/2008 |
| WO | WO2008125884 | 10/2008 |
| WO | WO2008157847 | 12/2008 |
| WO | WO2009000097 | 12/2008 |
| WO | WO2009083521 | 7/2009 |
| WO | WO2009083521 A3 | 7/2009 |
| WO | WO2009085058 | 7/2009 |
| WO | WO2009090648 | 7/2009 |
| WO | WO2009113910 | 9/2009 |
| WO | WO2010046238 | 4/2010 |
| WO | WO2011023582 | 3/2011 |
| WO | WO2011036048 | 3/2011 |
| WO | WO2011039630 | 4/2011 |
| WO | WO2011151169 A1 | 12/2011 |
| WO | WO2011151171 | 12/2011 |

OTHER PUBLICATIONS

Karabit et al, 1988, Studies on the evaluation of preservative efficacy III. The determination of antimicrobial characteristics of benzalkonium chloride, Int J of Pharmaceutics, 46, 141-147.

Kubo et al, 2008, Antimicrobial activity of anethole and related compounds from aniseed, Journal of the Science of Food and Agriculture, 88, 242-247.

Oyedemi et al., Apr. 6, 2009, The proposed mechanism of bactericidal action of eugenol, a-terpineol and y-terpinene against listeria monocytogened, *Streptococcus pyogenes, Proteurs vulgaris* and *Escherichia coli*, African Journal of Biotechnology, 8(7), 1280-1286.

Sato et al, 2006, Antimicrobial effect of trans-cinnamaldehyde, (–)-perillaldehyde, (–)-citronellal, citral, eugenol and carvacrol on airborne microbes using an airwasher, Biol Pharm bull, 29(11), 2292-2294.

Tippayatum et al, 2007, Antibacterial activities of thymol, eugenol and nisin against some food spoilage bacteria, Nat Science, 41, 319-323.

International Search Report PCT/EP2010/062982 dated Dec. 28, 2010.

Biologically Active Substances of Plant Origin, Russian Academy of Sciences, 2001.

Gablin, Balsamic fragrances Lemon thyme, Handmade Soaps, 2007, p. 84 with Translation.

(56) References Cited

OTHER PUBLICATIONS

Banayeva et al., Translation of "A Study of the Chemical Composiiton of the Essential Oil of Representatives of the Genus Thymus L. Growing in the Altai", Vegetable feed Chemistry, 1999, No. 3, pp. 41-48.

Banayeva et al., "A Study of The Chemical Composition of the Essential Oil of Representatives of the Genus Thymus L. Growing in the Altai", Vegetable feed Chemistry, 1999, No. 3, pp. 41-48.

Zhigzhitzhapova et al., Translation of "The Chemical Composition of the Essential Oil of Baikal Thyme, Thymus Baicalensis Serg., Growing in the Zabaikal Territory", Vegetable feed Chemistry, 2008, No. 1, pp. 73-76.

Zhigzhitzhapova et al., "The Chemical Composition of the Essential Oil of Baikal Thyme, Thymus Baicalensis Serg., Growing in the Zabaikal Territory", Vegetable feed Chemistry, 2008, No. 1, pp. 73-76.

Translation of Eurasian Written Opinion for Application No. 201100656 (PCT/EP2009/063081) dated Dec. 11, 2012.

Castor Oil, Wikipedia (website), 1-4, US, downloaded May 2, 2014.

Budavari (Editor), An Encyclopedia of Chemicals, Drugs, and Biologicals, The Merck Index, 1996, 1568, 12th Edition, Merck Research Laboratories, Whitehouse Station, US.

Umback et al., Georg Thieme Verlag, Kosmetik, 1995, 360-369, DE.

Henkel Opposition against EP Patent No. 2 348 838 B1 dated Feb. 7, 2014.

Biersdorf Opposition against EP Patent No. 2 348 838 B1 dated Feb. 6, 2014.

A. Perez-Vasquez et al., Antimicrobial activity and chemical composition of the essential oil of Hofmeisteria schaffneri, Journal of Pharmacy and Pharmacology, Aug. 5, 2010, 579-586, vol. 63.

Abdeslam Jaafari, Hassan Ait Mouse, El Mostapha Rakib et al, Chemical composition and antitumor activity of different wild varieties of Moroccan thyme, Brazilian Journal of Pharmacognosy, Aug. 27, 2007, 477-491, 17(4).

Achi, Composition and Antibacterial Activities of Tetrapleura tetraptera Taub, Research Journal of Microbiology, 2006, 416-422, vol. 1 No. 5, US.

Botelho et al, Antimicrobial activity of the essential oil from Lippia sidoides, carvacrol and thymol against oral pathogens, Brazilian Journal of Medical and Biological Research, 2007, 349-356, 40.

Cen Members, Chemical disinfectants and antiseptics—Quantitative suspension test for the evaluation of bactericidal activity of chemical . . . , European Standard, Jan. 1, 1997, 1-18, EN 1276.

Coco et al., Candida biofilms in denture stomatitis: novel detection and treatment methods, The Pan European Federation of the Internatnional Association for Dental Research, Sep. 11, 2008.

Davies A., Action of Biguanides, Phenols and detergents on *Escherichia coli* and its spheroplasts, Action of Biguanides, 1969, 233-243, 32.

Dimitrijevic, et al., A study of the synergistic antilisterial effects of a sub-lethal dose of lactic acid and essential oils, Food Chemistry, Jan. 1, 2007, 774-782, 104, Elsevier, US.

Evandro Leite De Souza, Interference of heating on the antimicrobial activity and chemical composition of Origanum vulgare L. (Lamiaceae) essential oil, Interference of heating on the antimicrobial activity and chemical composition of Origanum vulgare L. (Lamiaceae) essential oil, Apr. 1, 2008, 1-7, vol. 28, No. 2.

Figueredo et al, Studies of mediterranean oregano populations. VIII-Chemical composition of essential oils of oreganos of various origins, Flavour and Fragrance Journal, May 9, 2005, 134-139, 21.

Friedman, et al., Antibacterial Activities of Naturally Occurring Compounds Against Antibiotic-Resistant Bacilllus cereus, Journal of Food Protection, Mar. 12, 2004, 1774-1778, 67, No. 8, Journal of Food Protection, US.

Hong S, Antimicrobial Activity of Tyramine Derivatives, Antimicrobial Activity of Tyramine Derivatives, Oct. 29, 2000, NA, NA.

IPRP in PCTEP2012074399, Jul. 10, 2014, pp. 1-20, WO.

IPRP2 in PCTEP2012074409, Jul. 10, 2014.

IPRP2 in PCTEP2012074416, Jul. 10, 2014.

Jalali-Heravi et al, Analysis of Iranian rosemary essential oil: application of gas chromatography-mass spectrometry combined with chemometrics, Journal of Chromatography A, Mar. 21, 2011, 2569-2576, 1218.

Kirchner et al, Chemical composition and antimicrobial activity of Hedyosmum brasiliense Miq., Chloranthaceae, essential oil, Brazilian Journal of Pharmacognosy, Jan. 11, 2010, pp. 692-699; XP055036913, vol. 20 No. 5.

Kisgyorgy et al, Essential oil of the more important indigenous Thymus species occurring in the composition of Serpylli herba, Farmakognoziai Tansz., Jan. 1, 1983, 124-130, 29.

Leung A Y; Foster, Encyclopedia of common and natural ingredients used in food, drugs and cosmetics, Cinnamon (and Cassia), Jan. 1, 1996, pp. 167-170,260-264,393-397,405-408,492-494,510-511, ISBN: 978-0-471-50826-7.

M. Sebesan, Analysis of the I,II Essential Oils from Thyme (Thymus vulgaris L) and from Peppermint (Mentha piperita L), Analysis of the I,II Essential Oils from Thyme and from Peppermint, Dec. 31, 2008, 212-214, Retrieved from the Internet.

Mah J H, Paenibacillus tyraminigenes sp. nov. isolated from Myeolchi-jeotgal. A traditional Korean salted and fermented anchovy, Paenibacillus tyraminigenes sp. nov. isolated from Myeolchi-jeotgal., Oct. 31, 2008, pp. 209-214, vol. 127. No. 3.

Majnooni et al, Chemical composition, cytotoxicity and antioxidant activities of the essential oil from the leaves of citrus aurantium L., African Journal of Biotechnology, May 1, 2012, 498-503, 11(2).

Miladinovie et al, Investigation of the chemical composition—antibacterial activity relationship of essential oils by chemometric methods, Anal Bioanal Chem, Mar. 3, 2012, 1007-1018, 403.

Mintel, Antibacterial Fluride Toothpaste, Antibacterial Fluride Toothpaste, Nov. 2007, NA, NA, NZ.

Mintel, Mouth Rinse, Mouth Rinse, Oct. 2007, NA, NA, GB.

Naigre Ruth, Comparison of antimicrobial properties of monoterpenes and their carbonylated products, Comparison of antimicrobial properties of monoterpenes and their carbonylated products, 1996, 275-277, vol. 62, No. 3.

Rossi et al, Chemical fingerprinting and bioactivity of Amazonian Ecuador croton lechleri Mull. Arg. (Euphorbiaceae) stem bark essential oil: A new functional food ingredient?, Food Chemistry, Jun. 1, 2011, 837-848, 126.

Sagoo Sk, Chitosan potentiates the antimicrobial action of sodium benzoate on spoilage yeasts, Chitosan and Benzoate, Jan. 3, 2008, 168-172, 34—No. 3.

Sawamura et al, Characteristic odor components of citrus reticulata blance (Ponkan) cold-pressed oil, Biosci. Biotechnol. Biochem., Apr. 16, 2004, 1690-1697, 68(8).

Shixiang, Anticorrosive functions of convention flavors and fragrances, Toothpaste Industry, 2000, 23-27, 2, CN.

Singh et al., Antioxidant and antimicrobial activities of essential oil and various oleoresins of Elettaria cardamomum (seeds and pods), Journal of the Science of Food and Agriculture, Mar. 6, 2007, 280-289, 88.

Tian et al, Chemical composition and antifungal activity of essential oil from cicuta virosa L. var. latisecta celak, International Journal of Food Microbiology, Jan. 1, 2011, 464-470, 145.

Van Der Wolf, Disinfection of vegetable seed by treatment with essential oils, Seed Science and Technology, 2008, 76-88, 36, US.

Wang, Synergistric Antimicrobial Activities of Natural Oils with Chitosan Films, Journal of Agricultural and Food Chemistry, Oct. 29, 2011, 12411-12419, vol. 59 No. 23, ACS Publications, US.

Younhee Byun et al, Analysis of Composition and Activity of Essential Oil from Chrysanthemum zawadskii var. latilobum and C. indicum against Antibiotic-Resistant Pathobenic Bacteria, Natural Product Sciences, Jun. 16, 2008, 138-142, vol. 14-No. 2.

Yu et al., Chemical composition and antimicrobial activity of the essential oil of *Scutellaria barbata*, Phytochemistry 65 (2004), Sep. 5, 2003, 881-884, 65.

Zrira et al, Chemical composition of the essential oil of nine eucalyptus species growing in Morocco, Flavour and fragrance journal, Apr. 2, 2004, 172-175, 19.

(56) References Cited

OTHER PUBLICATIONS

Chialva et al., Qualitative Evaluation of Aromatic Herbs by Direct Headspace GC Analysis. Applications of the Method and Comparison with the Traditional Analysis of Essential Oils, Journal of high resolution chromatography, 1982, Created: Dec. 29, 2014—Lyudmyla Vaynerpp 182-188, 5, issue 4.

Joulain et al., The Absolute From flowers of Jasminum auriculatum Vahl from India, Flavour and Fragrance Journal, 1995, pp. 193-197, vol. 1.
Search Report in EP09175200, Feb. 8, 2010, EP.
Takeshi Deyama Etc., Studies on the Components of Essential Oil of Clove, Yakugaku Zasshi (Abstract), 1971, pp. 1383-1386, 91(12).
Written Opinion in EP09175200, Feb. 8, 2010, EP.
Written Opinion in PCTEP2010062982, Dec. 28, 2010.

* cited by examiner

DISINFECTING AGENT COMPRISING EUGENOL, TERPINEOL AND THYMOL

TECHNICAL FIELD

The present invention relates to a method of disinfecting a surface and to an antimicrobial composition. It particularly relates to an antimicrobial composition for personal cleaning, oral care, or hard surface cleaning.

BACKGROUND AND PRIOR ART

Sanitizing and disinfecting soap compositions comprising chlorine-based antimicrobial agent such as triclosan are known. Such compositions require rather long contact time to provide efficacious antimicrobial action. In practice, users, in particular children, do not spend long time in cleaning and as a result, cleaning with such compositions does not provide adequate prevention from surface or topical infection or adequate protection against diseases. The user, in spite of cleaning hands, is likely to have skin with relatively inadequate bacterial removal and may cause contamination of further animate and/or inanimate surfaces and lead to spreading of pathogens and consequent diseases. Users in general and children in particular who wash contaminated hands before meals with slow-acting antimicrobial compositions for relatively short time are at risk of contracting diseases. Further, many antimicrobial actives in addition to abrasives are included in oral care compositions like dentifrices but these actives generally require several minutes if not hours before effective antimicrobial action is effected. People often brush their teeth or rinse their mouth for very short period of time e.g. of the order of 1 minute or less thus making such compositions quite ineffective in providing the desired benefit.

Similarly in the area of hard surface cleaning e.g. cleaning of floors, table tops or utensils, the antimicrobial in the compositions are in contact with the substrate for less than a few minutes after which the surface is either wiped off or rinsed with water. These short time scales of cleaning action are ineffective in providing the desired benefit since most known antimicrobials commonly used in such products take several hours to provide the desired kill of microbes.

Therefore, there is a need of providing a composition that gives relatively more efficacious antimicrobial action when cleaning period is relatively small, typically about 5 minutes or less, preferably lesser than 2 minutes and in many cases less than one minute or sometimes as low as 15 seconds or lesser.

The present applicants, in WO10046238 have surprisingly found that compositions comprising selected ingredients, namely thymol and terpineol, in selective concentrations provide relatively quick antimicrobial action. They have continued their research to find more efficacious combinations of actives that not only provide the desired fast anti-microbial action but also enable this at lower concentrations. To their further surprise, they found that use of very small amounts of eugenol in combination thymol and terpineol enables the fast kinetics at much lower amount of thymol and terpineol than without eugenol.

Eugenol, terpineol and thymol are all components of essential oils and have been cited along with a host of other such essential oil components in prior publications.

JP2196718 (Kowa, 1989) discloses a liquid for external use having increased solubility and stability, containing 0.1 to 5% indomethacin and a 0.3 to 10% dissolution auxiliary as essential components, the dissolution auxiliary selected from limonene, pinene, camphene, cymene, citronellol, geraniol, nerol, linalool, terpineol, rhodinol, borneol, isoborneol, menthone, camphor, thymol, safrole, isosafrole, eugenol and isoeugenol.

JP19960080819 (Kao, 1996) discloses a composition for oral cavity, which contains the following (a) and (b) components besides (c)-(e) components. (a) capsules containing 0.1-20 wt. % of agar as a substance for forming a tunica and having an average grain size of 0.3-3 mm, (b) 0.0001-1% of more than one kind of perfumes selected from linalol, eugenol, anethole, terpineol, thymol, camphor, cinnamic alcohol, cinnamic aldehyde and cineol, (c) 0.1-1% of menthol, (d) a nonionic surfactant, and (e) an abrasive.

U.S. Pat. No. 6,613,728 (P & G, 2003) discloses a method of providing long-lasting disinfection to a hard surface, said method comprising the step of contacting said hard surface with a liquid disinfecting solution having a pH of from 2 to 6 and having low volatility, said liquid disinfecting solution comprising peroxygen bleach and an antimicrobial active selected from the group consisting of thymol, eugenol, menthol, geraniol, vertenone, eucalyptol, pinocarvone, cedrol, anethol, carvacrol, hinokitiol, berberine, ferulic acid, cinnamic acid, methyl salicylic acid, methyl salicylate, terpineol, limonene and mixtures thereof, and an anti-microbial compound having a vapor pressure of less than 0.1 mmHg when measured at 20° C., wherein said anti-microbial compound is selected from the group consisting of citric acid, benzoic acid, benzophenone, and mixtures thereof.

WO2006/053458 (Givaudan S A) discloses bactericidal formulations that come into contact with human body, particularly wash formulations including liquid soaps comprising perfume ingredients active against gram-negative bacteria.

None of the publications, cited above, teach that a small amount of eugenol when used along with a specified amount of a combination of thymol and terpineol provide for fast acting anti-microbial action, in a synergistic way.

It is an object of the present invention to overcome or ameliorate at least one of the disadvantages of the prior art, or to provide a useful alternative.

Another object of the present invention is to provide antimicrobial compositions that have relatively fast antimicrobial action.

SUMMARY OF THE INVENTION

According to one aspect of the present invention there is provided a method of disinfecting a surface comprising the steps of
   (i) applying a composition comprising:
      (a) 0.005 to 5% by weight eugenol;
      (b) 0.01 to 5% by weight terpineol;
      (c) 0.01 to 5% by weight thymol; and
      (d) a carrier;
   on to a surface; and
   (ii) rinsing the surface with a suitable solvent or wiping the surface with a suitable wipe.

According to another aspect of the present invention there is provided an antimicrobial composition comprising:
   (a) 0.005 to 5% by weight eugenol;
   (b) 0.01 to 5% by weight terpineol;
   (c) 0.01 to 5% by weight thymol;
   (d) 1 to 80% by weight an anionic surfactant; and
   (e) a carrier.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

The antimicrobial composition comprises eugenol, thymol, terpineol and a carrier. Various components of the antimicrobial composition are described below. The compositions of the present invention are preferred for non-therapeutic use, and more particularly preferred for use in cleaning surfaces of human body including skin, hair or oral cavity or for hard surface cleaning applications.

Eugenol

Eugenol is an allyl chain-substituted guaiacol. It is generally extracted from certain spices like clove or cinnamon. Eugenol has been used as a perfumery component, in preparing flavors, as an antiseptic or as a local anesthetic. The antimicrobial composition comprises 0.005 to 5%, preferably 0.02 to 1%, more preferably 0.03 to 0.4%, by weight eugenol. The composition of the invention is used such that, with dilution or otherwise, eugenol is in contact with the substrate at a concentration which is higher than 0.01 and lesser than 0.2% by weight of the composition. Without wishing to be bound by theory, it is believed that while the synergistic mixture of thymol and terpineol act as antimicrobial agents to impede the cellular function of the targeted microbes, eugenol acts synergistically as an efflux-pump inhibitor on the microbial cells at very low concentrations to enhance the efficacy of the terpineol-thymol mixture, thereby ensuring the antimicrobial action at lower concentrations of terpineol and thymol as compared to the mixture of terpineol-thymol without the use of eugenol.

Eugenol has the Structure:

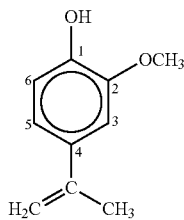

Thymol

The antimicrobial composition comprises 0.01 to 5%, preferably 0.02 to 1%, more preferably 0.03 to 0.4%, by weight thymol. The composition of the invention is used such that, with dilution or otherwise, thymol is in contact with the substrate at a concentration which is higher than 0.01 and lesser than 0.3% by weight of the composition. Thymol may be added to the antimicrobial composition in purified form.

Alternatively, thyme oil or thyme extract comprising thymol may be added to the antimicrobial composition, while ensuring that thymol is present in the desired concentration in the composition of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide*, and *Thymus citriodorus*.

The structure of thymol is given below:

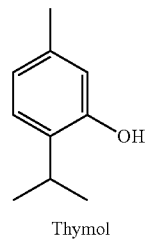

Thymol

Terpineol

The antimicrobial composition comprises 0.01 to 5% by weight terpineol, preferably 0.05 to 5%, more preferably 0.06 to 1%, and most preferably 0.06 to 0.6% by weight terpineol. The composition of the invention is used such that, with dilution or otherwise, terpineol is in contact with the substrate at a concentration which is higher than 0.05 and lesser than 0.3% by weight of the composition. The terpineol is preferably selected from alpha-terpineol, beta-terpineol, gamma-terpineol or mixtures thereof. It is particularly preferred that the terpineol is alpha-terpineol. Terpineol may be added to the antimicrobial composition in purified form.

Alternatively pine oil comprising terpineol may be added to the antimicrobial composition while ensuring that terpineol is present in the desired concentration in the composition of the present invention.

The structure of a terpineol compound is given below:

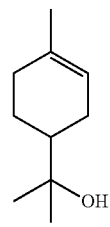

One advantage of including eugenol in the terpineol-thymol mixture is that while WO2006/053458 lists a large number of perfumery compounds which provide fast acting antibacterial action when used individually, the present inventors have ascertained that many of those perfumery compounds do not provide for synergistic action when used in combination as binary mixtures or ternary mixtures. This action has been found in the present invention. Another advantage of the present invention is that with the inclusion of eugenol, the concentration of thymol and terpineol could be reduced by about an order of magnitude to get the same fast acting antimicrobial action as compared to the activity obtained with thymol and terpineol alone (without the use of eugenol).

In areas like therapeutic or pesticidal or herbicidal applications the sensorial aspects are not critical. Unlike these areas, in the present invention, which is preferably a personal cleaning, oral care, or hard surface cleaning compositions, the low preferred concentration ranges of terpineol, thymol and eugenol are important since, the product is in contact with hands, mouth or other body parts, where the sensorial aspects like smell and skin feel are critical for consumer acceptability.

Carrier

The antimicrobial composition comprises a carrier. The carrier may be selected from the group consisting of water, oil, solvent, inorganic particulate material, starch, polymer or mixtures thereof. More preferred carriers are water, oil, inorganic particulate matter, or polymer. A more preferred carrier is water. The carrier is preferably from 0.1 to 99% by weight of the composition. The antimicrobial composition may be in form of a solid, liquid, gel, paste or soft solid and the carrier may be selected by a person skilled in the art depending on the format of the antimicrobial composition.

The examples of inorganic particulate materials include clay, talc, calcite, dolomite, silica, and aluminosilicate, more preferred being calcite, dolomite or silica. The examples of oils include mineral oils, vegetable oils, and petroleum-derived oils and waxes. The examples of solvents include alcohols, ethers and acetone.

The starch may be natural starch obtained from food grains or may be a modified starch.

Particularly preferred carriers are water or oil, more preferred carrier being a mixture of water and oil. However water/solvents mixtures may also be used. In such cases, a suitable solvent is an alcohol. Preferred alcohols are ethanol or iso-propyl alcohol. When alcohol is present in the composition, it is preferably present in 2 to 20% by weight of the composition.

In most of the envisaged applications like personal care/washing, oral care and hard surface cleaning, the antimicrobial composition may be formulated in an aqueous base water being carrier) e.g. products in gel format or in purely oil/solvent. However, most preferred product format has an emulsion base (water and oil being the carrier) e.g. soap products in liquid, solid, lotion or semisolid form for handwash, face wash, body wash, or shaving applications; toothpaste/dentifrices for oral care applications or products for hard surface cleaning in bars or liquids form.

Preferred carrier in the case of personal washing, hard surface cleaning and oral care application is water. In these applications the compositions are preferably not anhydrous.

Surfactant

The antimicrobial composition preferably comprises 1 to 80% surfactant. In general, the surfactants may be chosen from the surfactants described in well known textbooks like "Surface Active Agents" Vol. 1, by Schwartz & Perry, Interscience 1949, Vol. 2 by Schwartz, Perry & Berch, Interscience 1958, and/or the current edition of "McCutcheon's Emulsifiers and Detergents" published by Manufacturing Confectioners Company or in "Tenside-Taschenbuch", H. Stache, 2nd Edn., Carl Hauser Verlag, 1981. Any type of surfactant, i.e. anionic, cationic, nonionic, zwitterionic or amphoteric can be used.

A particularly preferred surfactant is soap. Soap is a suitable surfactant for personal washing applications of the antimicrobial composition of the invention. The soap is preferably C8-C24 soap, more preferably C10-C20 soap and most preferably C12-C16 soap. The soap may or may not have one or more carbon-carbon double bond or triple bond. The cation of the soap may be alkali metal, alkaline earth metal or ammonium. Preferably, the cation of the soap is selected from sodium, potassium or ammonium. More preferably the cation of the soap is sodium or potassium.

The soap may be obtained by saponifying a fat and/or a fatty acid. The fats or oils generally used in soap manufacture may be such as tallow, tallow stearines, palm oil, palm stearines, soya bean oil, fish oil, castor oil, rice bran oil, sunflower oil, coconut oil, babassu oil, palm kernel oil, and others. In the above process the fatty acids are derived from oils/fats selected from coconut, rice bran, groundnut, tallow, palm, palm kernel, cotton seed, soyabean, castor etc. The fatty acid soaps can also be synthetically prepared (e.g. by the oxidation of petroleum or by the hydrogenation of carbon monoxide by the Fischer-Tropsch process). Resin acids, such as those present in tall oil, may be used. Naphthenic acids are also suitable.

Tallow fatty acids can be derived from various animal sources and generally comprise about 1-8% myristic acid, about 21-32% palmitic acid, about 14-31% stearic acid, about 0-4% palmitoleic acid, about 36-50% oleic acid and about 0-5% linoleic acid. A typical distribution is about 2.5% myristic acid, about 29% palmitic acid, about 23% stearic acid, about 2% palmitoleic acid, about 41.5% oleic acid, and about 3% linoleic acid. Other similar mixtures, such as those from palm oil and those derived from various animal tallow and lard are also included.

Coconut oil refers to fatty acid mixtures having an approximate carbon chain length distribution of about 8% $C_8$, about 7% $C_{10}$, about 48% $C_{12}$, about 17% $C_{14}$, about 8% $C_{16}$, about 2% $C_{18}$, about 7% oleic and about 2% linoleic acids (the first six fatty acids listed being saturated). Other sources having similar carbon chain length distributions, such as palm kernel oil and babassu kernel oil, are included within the term coconut oil.

A typical fatty acid blend consisted of 5 to 30% coconut fatty acids and 70 to 95% fatty acids ex hardened rice bran oil. Fatty acids derived from other suitable oils/fats such as groundnut, soybean, tallow, palm, palm kernel, etc. may also be used in other desired proportions. The most preferred soap is a laurate soap. The soap, when present in solid forms of the present invention is present in an amount of 30 to 90%, preferably from 50 to 85%, more preferably 55 to 75% by weight of the composition. The soap, when present in liquid forms of the composition is present in 0.5 to 20%, preferably from 1 to 10% by weight of the composition.

The antimicrobial composition of the invention is useful in hard surface cleaning applications. In such applications preferred surfactants are non-ionic surfactants, such as C8-C22, preferably C8-C16 fatty alcohol ethoxylates, comprising between 1 and 8 ethylene oxide groups when the product is in the liquid form. When the product is in the solid form for hard surface cleaning applications surfactants are preferably selected from primary alkyl sulphate, secondary alkyl sulphonates, alkyl benzene sulphonates, or ethoxylated alkyl sulphates. The composition may further comprise an anionic surfactant, such as alkyl ether sulphate preferably those having between 1 and 3 ethylene oxide groups, either from natural or synthetic source and/or sulphonic acid. Especially preferred are sodium lauryl ether sulphates. Alkyl polyglucoside may also be present in the composition, preferably those having a carbon chain length between C6 and C16. Suitable surfactant concentrations in liquid forms of hard surface cleaning application are generally more than 0.5 but less than 10%, preferably from 1 to 5% by weight of the composition.

In solid compositions, the surfactant is preferably present in 5 to 40%, preferably from 10 to 30% by weight of the composition.

The antimicrobial composition of the invention is useful in oral care compositions e.g. in a dentifrice/toothpaste or oral rinse product. In such applications, preferred surfactants are anionic, non-ionic or amphoteric in nature, preferably anionic or amphoteric. The Anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear C10~C18 chain), and most preferably is cocoamidopropyl betaine (CAPB). Mixtures of amphoteric surfactants may also be employed. Suitable surfactant concentrations in oral care application are generally from about 2% to about 15%, preferably from about 2.2% to about 10%, more preferably from about 2.5 to about 5% by weight of the total composition.

Thus, in a highly preferred aspect, the antimicrobial compositions include soap, alkyl sulphate or linear alkyl benzene sulphonate as the surfactants.

The composition of the invention is especially suitable for use in a wash off process where the contact time of the antimicrobial actives with the surface is low, i.e of the order of less than 5 minutes, preferably less than 2 minutes, further more preferably less than a minute and in many cases less than 15 seconds.

A further additional advantage of the present invention is that it is observed that surfaces treated with a composition comprising terpineol, thymol, and eugenol surprisingly enable continued protection of the surface against growth of microbes for a substantial period of time thereafter.

Additional Ingredients

The composition may further comprise various additional ingredients known to a person skilled in the art. Such additional ingredients include but are not limited to: perfumes, pigments, preservative, emollients, sunscreens, emulsifiers, gelling agents, or thickening agents. The composition of the invention may also comprise antimicrobial actives in addition to eugenol, thymol and terpineol. Such antimicrobial actives may be trichlorocarbanilide (TCC), triclosan (TCN), a zinc compound e.g. (zinc pyrithione) or benzalkonium chloride (BKC), preferably benzalkonium chloride. Such additional antimicrobial active may be present in 0.1 to 5% by weight, preferably from 0.5 to 4% by weight of the composition.

Format

The antimicrobial composition may be in form of a solid, a liquid, a gel, or a paste. Alternately the composition can be in delivered on to surfaces in the form of a spray. A person skilled in the art can prepare compositions in various formats by choosing one or more carrier materials and/or surfactant. The antimicrobial compositions of the present invention are useful for cleansing and care, in particular for skin cleansing and skin care. It is envisaged that the antimicrobial composition can be used as a leave-on product or a wash-off product, preferably a wash-off product. The antimicrobial composition of the present invention can also be used for cleansing and care of hard surfaces such as glass, metal, plastic and the like. An especially useful way to deliver the composition of the invention on to hard surfaces is through the spray format.

According to one aspect, water is a preferred carrier. When water is the carrier, a preferred liquid composition comprises (a) 0.005 to 5% by weight eugenol;
(b) 0.01 to 5% by weight thymol,
(a) 0.01 to 5% by weight terpineol
(b) 10 to 99% by weight water, and;
(c) 0.1 to 30% by weight surfactant.

The liquid antimicrobial composition is useful for skin cleansing, in particular for hand wash or a face wash. Another very useful liquid antimicrobial composition is used for disinfecting hard surfaces, fabrics, nappies, skin surfaces which may be cut or scratched or on the cheeks and neck after shaving. Such liquid compositions are often called liquid antiseptic compositions and such compositions are often used after diluting with water. Suitable composition:water ratio for dilution is the range of 1:2 to 1:500 more preferably 1:10 to 1:400, further more preferably about 1:10 to 1:50. It is particularly preferred that such liquid antiseptic compositions comprise a cationic surfactant. Most preferred cationic surfactant is benzalkonium chloride. Benzalkonium chloride when included is preferably present in 1 to 10%, more preferably 1 to 5% by weight of the composition.

When water is the carrier, a preferred solid composition comprises:

(a) 0.005 to 5% by weight eugenol,
(b) 0.01 to 5% by weight thymol,
(c) 0.01 to 5% by weight terpineol,
(d) 5 to 30% by weight water, and;
(e) 30 to 90% by weight surfactant.

The solid antimicrobial composition is preferably in the form of a shaped solid, more preferably a bar. The solid antimicrobial composition is particularly useful for skin cleansing in particular for hand wash or a face wash. In the solid antimicrobial composition the surfactant is preferably soap.

According to another aspect, inorganic particulate material is also a suitable carrier. When inorganic particulate material is the carrier, the antimicrobial composition is in a solid form. Preferably the inorganic particulate material is talc. When the inorganic particulate material is talc, the solid antimicrobial composition is particularly useful as a talcum powder for application on face or body.

According to a further aspect, solvent is a preferred carrier. Although any solvent can be used, alcohol is a preferred solvent. Short chain alcohols, in particular ethanol and propanol are particularly preferred as carrier for an antimicrobial wipe or an antimicrobial hand sanitizer composition.

According to an aspect of the present invention there is provided a method of disinfecting a surface comprising the steps of (i) applying a composition comprising: (a) 0.005 to 5% by weight eugenol; (b) 0.01 to 5% by weight terpineol; (c) 0.01 to 5% by weight thymol; and (d) a carrier; on to a surface; and (ii) rinsing the surface with a suitable solvent or wiping the surface with a suitable wipe.

The solvent for rinsing the surface is preferably water but could also be a mixture of water and alcohol. The word "rinsing" herein includes the act of wiping the surface with a suitable wipe. Thus, the surface e.g hand, face, body, oral cavity, or any hard surface e.g. a utensil is first contacted with the composition of the invention. It is then rinsed preferably with sufficient amounts of water after a pre-determined period of time to remove any visible or sensory reside of the composition. Alternately an alcohol wipe or a water/alcohol impregnated wipe may be used to wipe the surface to be visibly free of the anti-microbial composition. The step of rinsing the substrate is preferably carried out less than 5 minutes, preferably less than 2 minutes, further more preferably less than a minute and in many cases less than 15 seconds after the step of applying the composition on the substrate.

The method of disinfecting the surface preferably comprises applying a composition comprising (a) 0.03 to 0.4% by weight eugenol; (b) 0.03 to 0.6% by weight thymol; 0.06 to 1.5% by weight terpineol; and a carrier on to the surface before the step of rinsing or wiping. The composition useful in the disinfection method preferably comprises 1 to 80% surfactant. The surfactant is preferably anionic. Another aspect provides for the surfactant to be cationic. The cationic surfactant is preferably benzalkonium chloride. When present benzalkonium chloride is preferably 0.1 to 5% by weight of the composition.

According to a preferred aspect, the invention provides for non-therapeutic benefits.

Thus, according to yet another aspect of the invention there is provided use of a composition comprising 0.005 to 5% eugenol; 0.01 to 5% by weight thymol, 0.01 to 5% by weight terpineol, and a carrier for faster reduction in microbial count.

According to yet another aspect of the invention there is provided use of a composition comprising 0.005 to 5% by weight eugenol, 0.01 to 5% by weight thymol, 0.01 to 5% by weight terpineol, and a carrier for improved hygiene of surfaces of human body. Human surfaces include skin, hands and oral cavity.

The invention thus provides for use of a composition comprising 0.005 to 5% by weight eugenol, 0.01 to 5% by weight thymol, 0.01 to 5% by weight terpineol, and a carrier for improved hand hygiene.

The invention also provides for use of a composition comprising 0.005 to 5% by weight eugenol, 0.01 to 5% by weight thymol, 0.01 to 5% by weight terpineol, and a carrier for improved oral hygiene.

The invention further provides for use of a composition comprising 0.005 to 5% by weight eugenol, 0.01 to 5% by weight thymol, 0.01 to 5% by weight terpineol, and a carrier for improved hard surface hygiene.

The invention also provides for therapeutic benefits.

Thus, according to yet another aspect of the invention there is provided a composition comprising 0.005 to 5% by weight eugenol, 0.01 to 5% by weight thymol, 0.01 to 5% by weight terpineol, and a carrier for faster reduction in microbial count.

EXAMPLES

The invention will now be demonstrated with examples. The examples are for purpose of illustration only and do not limit the scope of claims in any manner.

Examples 1 to 3

Synergistic Interaction Between Eugenol and a Combination of Thymol and Terpineol in Providing Bacterial Kill in Short Time Frames (15 Seconds)

Compositions comprising active/actives were prepared with water as a carrier as shown in Table 1 below. Terpineol, thymol and eugenol were obtained from Nishant aromas, India.

About $10^7$ bacterial cells (*E. coli* ATCC 10536) were taken in a test tube and contacted with various compositions for a period of 15 seconds. Bacteria were taken out after 15 seconds of contact and presence of viable cells was determined by neutralization of the antimicrobial, serial dilution and plating on agar plates. The data is presented in Table-1 as log (Viable *E. Coli*) which is the $\log_{10}$ of the number of viable *E. coli* remaining after 15 seconds of contact. Thus if $10^4$ remained, log (Viable *E. coli*) is 4.

The data in Table-1 is an average result of four experiments.

TABLE 1

Antimicrobial efficacy of eugenol in combination with thymol and terpineol

| Ex No | Composition | Log (Viable *E. coli*) |
|---|---|---|
| 1 | Eugenol (0.05%) | 7.0 |
| 2 | Thymol (0.033%) + Terpineol (0.08%) | 2.8 |
| 3 | Eugenol (0.05%) + Thymol (0.033%) + Terpineol (0.08%) | No viable bacteria remaining |

The data in Table-1 indicates that there is a synergistic interaction when eugenol is used along with a combination of thymol and terpineol in providing antibacterial kill in very short time frames.

Example 4 to 7

Antibacterial Efficacy of Thymol, Terpineol and their Combination with Eugenol

Various compositions as shown in Table-2 were prepared using the same procedure as used for examples 1 to 3 and the antibacterial efficacy was evaluated using the same procedure as used to evaluate Examples 1 to 3. The data on antibacterial efficacy is represented in Table-2.

TABLE 2

| Ex No | Composition | Log (Viable *E. coli*) |
|---|---|---|
| 4 | Thymol (0.025%) + Eugenol (0.1%) | 6.5 |
| 5 | Terpineol (0.065%) + Eugenol (0.1%) | 6.5 |
| 6 | Thymol (0.025%) | 6.5 |
| 7. | Terpineol (0.065%) | 6.5 |

The data in Table-2 read along with data in Table-1 indicates that each of the three ingredients thymol, terpineol, or eugenol individually or any of their binary mixtures are unable to provide as good an antibacterial action as a ternary mixture of the three ingredients. In fact the data indicates synergistic antibacterial efficacy.

Examples 8 to 10

Antimicrobial Efficacy of Another Composition of the Invention

Compositions as summarized in Table-3 were prepared using a similar procedure as used for Examples 1 to 3 and the antibacterial efficacy was evaluated using a procedure similar to that used for Examples 1 to 3. The data is summarized in Table-3.

TABLE 3

| Ex No | Composition | Log (Viable *E. coli*) |
|---|---|---|
| 8 | Thymol (0.025%) + Terpineol (0.0625%) | 5.86 |
| 9 | Eugenol (0.05%) | 6.95 |
| 10 | Thymol (0.025%) + Terpineol (0.0625%) + Eugenol (0.05%) | 0.93 |

The data in Table-3 indicates that similar synergy is observed with another set of concentrations (lower concentrations than used in Table-1) of thymol, terpineol, and eugenol.

Examples 11 to 13

Liquid Antiseptic Compositions Comprising Benzalkonium Chloride

Liquid antiseptic compositions as shown in Table-4 were prepared. The various compositions were diluted with water in a ratio of composition:water of 1:400 and then tested for antibacterial efficacy. The procedure used was similar to that used for Examples 1 to 3. The data on antibacterial efficacy is summarized in Table-4.

TABLE 4

Liquid antiseptic compositions.

| Ingredient | Example - 11 Weight % | Example - 12 Weight % | Example - 13 Weight % |
| --- | --- | --- | --- |
| Thymol | 0.5 | — | 0.5 |
| Terpineol | 1.0 | — | 1.0 |
| Eungenol | 0.1 | — | 0.1 |
| Benzalkonium chloride | — | 3.0 | 3.0 |
| Water | To 100 | To 100 | To 100 |
| Log (Viable E. Coli) | 6.9 | 5.5 | 4.7 |

The data in Table-4 indicates that a combination of terpineol, thymol and eugenol interact synergistically with benzalkonium chloride to provide vastly improved antibacterial efficacy.

Example-14 to 16

Soap Bar Composition

Soap bar compositions were prepared as per conventional procedure for preparing milled and plodded soap bars. The compositions of the various soap bars are summarized in Table-5. Solutions of the soap bars at 8% concentration in water were prepared and used to test antibacterial efficacy using a procedure similar to that used for Examples 1 to 3 except that $10^6$ viable bacteria were used. The data is summarized in Table-5.

TABLE 5

Soap bars

| Ingredient | Example 14 | Example 15 | Example 16 |
| --- | --- | --- | --- |
| Sodium Soap TFM = 74 | 79.92 | 79.92 | 79.92 |
| Glycerine | 2.00 | 2.00 | 2.00 |
| Salt | 0.70 | 0.70 | 0.70 |
| Soda Ash | 0.25 | 0.25 | 0.25 |
| EDTA tetra sodium | 0.04 | 0.04 | 0.04 |
| DTPA | 0.05 | 0.05 | 0.05 |
| Thymol | — | 0.20 | 0.20 |
| Terpeniol | — | 0.50 | 0.50 |
| Eugenol | — | — | 0.09 |
| TCC | 0.05 | — | — |
| Water | To 100 | To 100 | To 100 |
| Log (Viable E. Coli) | 4.50 | 3.57 | 3.26 |

The data in Table-5 indicates that soap with thymol and terpineol provides for 10 times better bacteria removal as compared to a conventional antibacterial soap (containing TCC ie. Trichlorocarbanilide). As compared to this, a soap bar of the present invention additionally comprising eugenol (Example-16) provides for 20 times better bacteria removal.

Example 17

Oral Care Composition

Good antibacterial oral care compositions were prepared as shown in Table-6.

TABLE 6

| Ingredient | Concentration (wt %) |
| --- | --- |
| Calcium carbonate | 40.0 |
| Sorbitol(70% solution) | 15.0 |
| Sodium lauryl sulphate | 2.5 |
| Silica hydrated | 5.0 |
| Potassium nitrate | 0.5 |
| SCMC | 0.625 |
| Sodium monofluorophosphate | 0.76 |
| Sodium saccharin | 0.25 |
| Neutral Sodium silicate | 1.75 |
| Thymol | 0.2 |
| Terpineol | 0.5 |
| Eugenol | 0.09 |
| Water | To 100 |

The invention claimed is:

1. A method of disinfecting a surface comprising the steps of
   (i) applying a composition comprising:
      (a) 0.005 to 5% by weight eugenol;
      (b) 0.01 to 5% by weight terpineol;
      (c) 0.01 to 5% by weight thymol; and
      (d) a carrier comprising water;
   on to a surface; and
   (ii) rinsing the surface with a suitable solvent or wiping the surface with a suitable wipe.

2. A method of disinfecting a surface as claimed in claim 1, wherein the treatment is non-therapeutic.

3. A method as claimed in claim 1 wherein said step of rinsing or wiping the surface is carried out less than 5 minutes after the step of applying the composition on the surface.

4. A method as claimed in claim wherein said composition comprises
   a. 0.03 to 0.4% by weight eugenol;
   b. 0.03 to 0.6% by weight thymol;
   c. 0.06 to 1.5% by weight terpineol; and
   d. a carrier comprising water.

5. A method as claimed in claim 1 comprising 1 to 80% surfactant.

6. A method as claimed in claim 5 wherein said surfactant is anionic.

7. A method as claimed in claim 1 wherein said composition comprises benzalkonium chloride.

8. An antimicrobial composition comprising:
a. 0.005 to 5% by weight eugenol;
b. 0.01 to 5% by weight terpineol;
c. 0.01 to 5% by weight thymol;
d. 1 to 80% by weight of a surfactant; and
e. a carrier comprising water wherein the composition is a personal wash, oral care or hard surface cleaning composition.

9. An antimicrobial composition as claimed in claim 8 comprising:
a. 0.005 to 5% by weight eugenol;
b. 0.01 to 5% by weight thymol;
c. 0.01 to 5% by weight terpineol;
d. 10 to 99% by weight water; and
e. 1 to 30% by weight surfactant wherein the composition is a liquid.

10. An antimicrobial composition according to claim 9 that further comprises 1 to 5% by weight benzalkonium chloride.

11. An antimicrobial composition as claimed in claim 9 wherein said surfactant is a cationic surfactant.

12. An antimicrobial composition as claimed in claim 8 comprising:
a. 0.005 to 5% by weight eugenol;
b. 0.01 to 5% by weight thymol;
c. 0.01 to 5% by weight terpineol;
d. 5 to 30% by weight water; and
e. 30 to 80% by weight surfactant wherein the composition is a shaped solid.

13. An antimicrobial composition as claimed in claim 12 wherein said surfactant is soap.

14. An antimicrobial composition according to claim 8 wherein the composition comprises:
a 0.03 to 0.4% by weight eugenol;
b, 0.06 to 0.6% by weight terpineol;
c. 0.03 to 0.4% by weight thymol;
d. 1 to 80% by weight of a surfactant; and
e. a carrier comprising water.

15. An antimicrobial composition according to claim 8 that is a wash-off product.

16. An antimicrobial composition according to claim 8 that is a personal wash or oral care composition.

\* \* \* \* \*